United States Patent [19]

Pochodylo

[11] Patent Number: 4,840,899
[45] Date of Patent: Jun. 20, 1989

[54] METHOD FOR THE PRODUCTION OF RIBAVIRIN USING HIGH ROBOSE DONOR CONCENTRATIONS

[75] Inventor: James M. Pochodylo, Rochester, N.Y.

[73] Assignee: Eastman Kodak Company, Rochester, N.Y.

[21] Appl. No.: 97,767

[22] Filed: Sep. 17, 1987

[51] Int. Cl.$^4$ .................. C12P 19/35; C12P 19/28; C12R 1/13
[52] U.S. Cl. ........................... 435/87; 435/85; 435/840
[58] Field of Search ............... 435/85, 840, 87

[56] References Cited

U.S. PATENT DOCUMENTS

| | | | |
|---|---|---|---|
| 3,976,545 | 8/1976 | Witkowski et al. | 195/28 |
| 4,458,016 | 7/1984 | Yamanaka et al. | 435/85 |
| 4,614,719 | 9/1986 | Fujishima et al. | 435/85 |

OTHER PUBLICATIONS

U.S. Ser. No. 97,762 filed 9/17/87, Lievense et al.
Derwent Abs 77-76390 Y/43 J50123883, (9-1975), Kyowa.
Derwent Abs 84-291215/47 J59179094, (10-1984), Yamasa.
Biotech 88-11277 J63177797, (Jul. 1988).
Biotech 88-05074 Agrig. Biol. Chem., (1988), 52,1,295-296.
Biotech 88-10183 Agrig. Bio. Chem., (1988), 52,7,1777-83.
Biotech 88-08418 Agric. Biol. Chem., (1988), 52,5,1233-37.

*Primary Examiner*—Herbert J. Lilling
*Attorney, Agent, or Firm*—J. Jeffrey Hawley

[57] ABSTRACT

A method for the production of a 1,2,4-triazole nucleoside comprising the step of reacting a ribose donor with a triazole compound in the presence of an enzyme preparation derived from *Brevibacterium acetylicum* is disclosed. The method is characterized in that the ribose donor is guanosine; the concentration of the donor is above about 100 mM; and the enzyme preparation is added before the reaction mixture gells. The method is capable of high production rates and high concentration of the final product.

6 Claims, No Drawings

METHOD FOR THE PRODUCTION OF RIBAVIRIN USING HIGH ROBOSE DONOR CONCENTRATIONS

BACKGROUND OF THE INVENTION

The present invention is directed to a method for the production of ribavirin and related compounds. The systematic name for ribavirin is 1-β-D-ribofuranosyl-1,2,4-triazole-3-carboxamide. Compounds of this type are known antiviral agents. Reference is made to U.S. Pat. No. 3,798,209 of Joseph T. Witkowski et al issued Mar. 19, 1974. Throughout the present specification, reference will be made to ribavirin. It will be understood that related compounds having a ribose group attached to a triazole are also intended.

There are several methods for the production of ribavirin. Chemical methods (those methods not using enzymes) are expensive. Expensive starting materials ad process steps characterized by low yields are common.

As a result, bioconversion methods have been extensively studied. In these methods, an enzyme or enzymes are used to attach the ribose to the triazole. In some cases, the enzyme is first isolated and then used as the catalyst. Reference is made to U.S. Pat. No. 3,976,545 of Witkowski et al issued Aug 24, 1976. In this patent there is disclosed a method wherein the ribose donor is ribose-1-phosphate. The triazole acceptor 1,2,4-triazole-3-carboxamide is reacted with the donor in the presence of nucleoside phosphorylase at a temperature between 0° C. and 50° C. The source of the enzyme is broadly disclosed.

Methods involving fermentation are also well known. In these methods the 1,2,4-triazole-3-carboxamide is added to a culture medium containing proliferating microorganisms such as a microorganism from the genus Brevibacterium. In this case, the necessary ribose donor comes from the fermentation medium as the organisms grow. Since the organisms are growing, the temperature is relatively low. Typical temperature s are between 20° C. and 40° C. Reaction times are very long, typically on the order of days.

In U.S. Pat. No. 4,458,016 to Yamanaka et al issued July 3, 1984 there is described a method that is very similar to the method of U.S. Pat No. 3,976,545 discussed above except that the temperature is between 55° and 65° C. Rather than isolated enzyme, whole cells containing the necessary activity can be used. Comparative results in the specification of this patent with the specific materials used indicate that the amount of ribavirin that is produced is very low at 70° C. and negligible at 75° C. and 80° C. (see table 3 at column 7) The microorganism that was used in this test was Klebsiella pneuminiae and the ribose donr was either ribose-1-phosphate or uridine.

In U.S. Pat. No. 4,614,719 to Fujishima et al issued Sept. 30, 1986 there is disclosed a method that is similar to the method of U.S. Pat. No. 4,458,016 patent discussed above. In U.S. Pat. No. 4,614,719 patent a *Brevibacterium acetylicum* microorganism is used under non-proliferative conditions. A wide variety of ribose donors can be used according to this disclosure and the temperature can be between 40° C. and 80° C. However, in the examples, inosine is predominantly used as the donor and the temperature is usually 60° C. In example 2 a variety of donors are tested wth the *B. actylicum* at 60° C. and in Example 4 a variety of temperatures up to 70° C. are tested with that microorganism and inosine as the donor. The yield of ribavirin dramatically decreases between 65° and 70° C.

The bioconversion method of U.S. Pat. No. 4,458,016 and U.S. Pat. No. 4,614,719 offer many advantages over the previous chemical method and the methods where the enzyme had to be isolated before use. However, additional improvements were still needed. For example, these methods produce ribavirin at a rate that is slower than desired. In U.S. Pat. No. 4,614,719 examples, the typical reaction time is 20 or 24 hours and the amount of ribavirin produced is relatively low. (Calculated to be at most about 10 g/L based on the data given.) Thus, while the % yield (actually the % conversion as described below) might be acceptable in these methods, the productivity of these methods is less than desired. Further, since the ribavirin is produced in only dilute solution, the recovery is more expensive than desired.

SUMMARY OF THE INVENTION

In accordance with the present invention there is provided an improved method for the production of a 1,2,4-triazole nucleoside comprising the step of reacting a ribose doner with a triazole compound in the presence of an enzyme preparation derived from *Brevibacterium acetylicum*. The improvement according to the present invention is that the ribose donor is guanosine or a guanosine derivative; the concentration of the donor is above about 100 mM (millimolal); and the enzyme preparation is added before the reaction mixture gels. The method according to this invention is capable of achieving higher concentrations of the desired product in the reaction mixture.

In the typical method, the enzyme preparation is separated from the reaction mixture and discarded. I have found that significant amounts of the desired product are associated with the enzyme preparation. In a preferred embodiment of this invention, the enzyme preparation is separated from the reaction mixture and is washed so as to recover additional product.

In accordance with a further improvement of the method, there is provided the additional step of adding the ribose donor and the triazole during the course of the reaction. This method is capable of producing ribavirin and related compounds in very high concentrations.

DETAILED DESCRIPTION OF THE INVENTION

The final concentration of the ribavirin in the reaction mixture is an important component of the overall cost of carrying out the method. High concentrations allow for better economics since the recovery from concentrated solutions is less expensive than from dilute solutions. Using the method of the present invention, very high ribavirin concentrations, on the order of 100 g/L in preferred embodiments, can easily be achieved.

In accordance with preferred embodiments of the present invention, the temperature should be at or above 65° C. during at least part of the method. Any temperature above this limit can be used but as a practical matter, the conversion does decrease as the temperature increases, even though the rate of production remains high. Thus, a temperature of about 70° C. is preferred.

The ribose donor is guanosine. It can be purchased commercially and is found in the hydrolysate of RNA, for example yeast RNA. Derivatives of guanosine can also be used such as guanylic acid.

The microorganism that is employed as the source of the catalytic activity is a *Brevibacterium acetylicum*. Any strain of this species can be used. The strain identified as ATCC 39311 available from The American Type Culture Collection and which is described in U.S. Pat. No. 4,614,719 referenced above is preferred.

The microorganism can be prepared by conventional fermentation processes such as the process described in Preparation 1 just prior to the present examples. A sample of the microorganism is inoculated into a fermentor with suitable nutrients and caused to grow to a stationary phase. The resulting fermentation broth can be used directly as the catalytic material. The cells can also be removed from the broth by filtration or centrifugation and used as a cell paste. The cells can be treated so as to increase their permeability. Treatments such as freeze thawiing, and other treatments described in U.S. Pat. No. 4,614,719 patent are useful for this purpose.

According to the present invention any enzyme preparation that is derived from *B. acetylicum* is useful. This includes the preparations described above and also any preparations from microorganisms that express the gene or genes isolated from *B. acetylicum* that is responsible for the nucleoside phosphorylase activity of this microorganism.

The starting pH can also vary widely and can range between about 6.0 and 9.2. While it is not critical to control the pH during the reaction, pH control is desirable. The optimum pH for ribavirin production is about 7.2.

According to the invention, the concentration of the starting materials is higher than that usually found in similar methods. For example, guanosine is present in an amount of between 100 mM and 200 mM while the triazole is present in an amount of between 100 mM and 200 mM. In contrast, the highest concentration of the donor in the U.S. Pat. No. 4,614,719 patent cited above is about 50 mM.

I have found that reaction mixtures using the donor guanosine tend to gel at high concentrations of guanosine at relatively high temperatures. Accordingly, catalyst is added before gelling occurs. Thus, the catalyst (enzyme preparation) can be first mixed with one of the reagents and the other of the reagents added to that mixture. As the other reagent is added, the reaction begins immediately thereby preventing gel formation. Alternatively, the reactants can be mixed at low temperature and the catalyst added as the temperature is increased but before gelling occurs. These procedures are not suggested in the references cited above. In U.S. Pat. No. 4,614,719 patent, for example, the reagent mixture is first formed and the catalyst is added to that mixture.

In a particularly preferred embodiment, ribose donor and triazole are added during the course of the reaction. These reagents can be added continuously or in batches over time for example, every eight hours. The rate of addition is preferably about 40 mM/hour although higher and lower rates can be used. As noted previously, concentrations of ribavirin near 100 g/L can be achieved over the course of the reaction. Depending on the desired ending concentration, the time of reaction can vary widely, for example between about 6 to 30 hours.

In addition to the ribose donor and the triazole, the reaction mixture preferably contains phosphhate ion as this may be required by the enzymes. A useful source of phosphate ions is potassium monophosphate and the concentration is typically between about 25 mM and 100 mM. Lower levels of phosphate are useful if the pH is controlled during the reaction.

In the conventional methods of the present type, the cells that are used as the catalyst are removed from the reaction mixture and discarded. I have found that these cells contain a significant amount of the desired product. Thus, in a preferred method, the enzyme preparation is recovered, such as by centrifugation and washed. Additional product is then recovered from the wash liquid. The wash liquid is preferably water.

In the examples below, the % conversion is referred to. The % conversion is the amount of ribavirin, on a molar basis, divided by the initial amount of starting materials, based on the molar amount of the limiting reactant. This is believed to be referred to as yield in the prior art references. More precisely, yield refers to the amount of product produced divided by the amount of starting material that reacts. To calculate yield, the final amount of starting material must be known. In the present examples, no effort was made to measure the remaining amount of starting material at the end of the reaction. If the starting materials go only to the desired product, then % conversion and % yield are the same.

The following preparation and examples are submitted for a further understanding of the invention.

PREPARATION 1

Preparation of: *Brevibacterium acetylicum*

Ten liters of an aqueous cultivation medium at pH 7.2 was prepared. sterilized, and combined in a fermentor. The composition of the medium is shown in Table I. An inoculum was prepared by culturing *Brevibacterium acetylicum* ATCC 39311 in a Fernbach flask containing 500 mL of medium for 20 hours at 30° C. The Fernbach medium was identical to that used in the fermentor, except it lacked magnesium sulfate. After transfer of the inoculum, the fermentor was cultured at 30° C. for 20 hours. The pH was controlled at 7.2 with potassium hydroxide. Additional glucose, amounting to 20 g/L of broth, was added at 12 hours into the fermentation.

At the end of the fermentation, centrifugation of the broth yielded 50 grams of wet cells per liter of broth. The cells were washed by re-suspending them in a 10mM Phosphate buffer. They were then collected by centrifugation and stored as a frozen paste.

TABLE I

| Fermentation Medium | | |
|---|---|---|
| | Component | Concentration (g/L) |
| 1. | Nutrient broth | 20 |
| 2. | $K_2HPO_4$ | 14 |
| 3. | $KH_2PO_4$ | 5.5 |
| 4. | Sodium citrate | 0.025 |
| 5. | $MnCl_2.4H_2O$ | 0.015 |
| 6. | $ZnCl_2$ | 0.01 |
| 7. | $FeCl_3.6H_2O$ | 0.01 |
| 8. | $MgCl_2.6H_2O$ | 0.25 |
| 9. | $CuCl_2.2H_2O$ | 0.001 |
| 10. | $CaCl_2.2H_2O$ | 0.00375 |
| 11. | $CoCl_2.2H_2O$ | 0.001 |
| 12. | $NaMoO_4.2H_2O$ | 0.0005 |
| 13. | Polyglycol P-2000* | 2 |
| 14. | Glucose | 50 |
| 15. | $MgSO_4.7H_2O$ | 0.75 |
| 16. | Thiamine.HCl | 0.0002 |
| 17. | p-Aminobenzoic acid | ·0.0002 |
| 18. | Pyridoxine.HCl | 0.0002 |

TABLE I-continued

| | Fermentation Medium | |
|---|---|---|
| | Component | Concentration (g/L) |
| 19. | Nicotinic acid | 0.0002 |
| 20. | Riboflavin | 0.0002 |
| 21. | Calcium d-pantothenate | 0.0002 |
| 22. | Folic acid | 0.000002 |

*available from Dow Chemical Midland Mich. USA

EXAMPLE 1

Gel Prevention and Cell Washing (A) Comparison

Bioconversion media were prepared by combining various amounts of guanosine and 1,2,4-triazole-3-carboxamide. The amounts were 20, 40, or 100 millimoles. The two reactants were used in a 1:1 molar ratio. The reaction mixture also contained 20 millimoles of $KH_2PO_4$ and 200 mL water. Forty grams of the *B. acetylicum* cell paste were added to initiate the bioconversion. The initial pH of each flask was adjusted to pH 7.2 with potassium hydroxide.

The flask with 100 millimoles of the two reactants gelled as it was heated to 70° C.—before any cell paste was added. The flask with 40 millimoles of the two reactants also gelled, but required a few minutes longer. Agitation via the stir bar was ineffective in reversing the gelling in both cases.

(B)

Bioconversion media were prepared as above, except the concentration of guanosine and 1,2,4-triazole-3-carboxamide were varied from 100 to 200 mM. The two reactants were used in a 1:1 molar ratio. The initial pH of each flask was adjusted to pH 7.2 with potassium hydroxide. The bioconversions were carried out at 70° C. The cells were added promptly as the temperature reached 70° C. to avoid gelling of the bioconversion mixture.

The final conversion was determined at 24 hours. Each bioconversion broth was centrifuged, and samples were taken from the supernatant for determination of the final, cell-free ribavirin concentration.

The cell paste from each bioconversion (about 40 grams) was re-suspended in 200 mL water These solutions were stirred at 22° C. for 1 hour to extract ribavirin from the cells. The solutions were then centrifuged, and samples were taken from the supernatant for determination of the extracted ribavirin. The extraction process was repeated a second time using fresh water and the cell paste from the first extraction.

The initial reaction rate calculated over the first hour of the bioconversion, the cell-free ribavirin concentration and conversion after seven hours of reaction, and the final, cell-free ribavirin concentration and conversion, are shown in Table II as a function of the initial guanosine concentration in the cell-free solution. The increase in the final conversion obtained by extracting ribavirin from the cells is shown in Table III.

TABLE II

Ribavirin Production as a Function of Initial Guanosine and 1,2,4-triazole-3-carboxamide Concentrations Between 100 and 200 mM

| Initial Guanosine Concen. (mM) | Initial Rate of Ribavirin Production (g/L/Hr.) | Ribavirin Conc. (g/L) 7 Hr. | Ribavirin Conc. (g/L) Final | % Conversion 7 Hr. | % Conversion Final |
|---|---|---|---|---|---|
| 100 | 3.9 | 14.8 | 16.8 | 61 | 70 |
| 125 | 4.5 | 18.8 | 20.9 | 62 | 70 |
| 150 | 5.4 | 22.7 | 25.1 | 62 | 70 |
| 175 | 5.4 | 25.7 | 28.9 | 60 | 68 |
| 200 | 5.5 | 28.3 | 32.8 | 58 | 68 |

TABLE III

Impact of Extraction of Ribavirin from Cells on the Final Conversion

| Initial Guanosine Concen. (mM) | Final Conversion (%) No Extraction | Final Conversion (%) One Extraction | Final Conversion (%) Two Extractions |
|---|---|---|---|
| 100 | 70 | 78 | 79 |
| 125 | 70 | 79 | 80 |
| 150 | 70 | 79 | 80 |
| 175 | 68 | 77 | 78 |
| 200 | 68 | 77 | 79 |

EXAMPLE 2

Accumulation of Ribavirin to a High Concentration using a Fed-batch Bioconversion Bioconversion media were prepared as in Example 1, except the initial amounts of guanosine and 1,2,4-triazole-3-carboxamide were 40 millimoles. The initial pH of each flask was adjusted to pH 7.2 with potassium hydroxide. The bioconversions were initiated as in Example 1. The cells were added promptly as the temperature reached 70° C. to avoid gelling of the bioconversion mixture. Forty millimole additions of both guanosine and 1,2,4-triazole-3-carboxamide were made at 6 and 12 hours into the bioconversion. Thus after the second addition, a total of 120 millimoles of the two reactants had been added. Potassium hydroxide was added at 6 hours to adjust the pH from 6.7 to 7.2.

The cell-free ribavirin concentration, the conversion based on guanosine, and the overall reaction rate at 6, 12, and 24 hours are shown in Table VII.

TABLE VII

Performance of the Fed-batch Bioconversion

| Time (Hrs) | Ribavirin Conc. (g/L) | Average Production Rate (g/L/Hr.) | % Conversion |
|---|---|---|---|
| 0 | 0 | 0 | 0 |
| 6 | 25.8 | 4.3 | 53 |
| 12 | 56.7 | 4.7 | 58 |
| 24 | 94.9 | 4.0 | 65 |

EXAMPLE 3

Batch Conversion with 500 mM Guanosine and 1,2,4-triazole-3-carboxamide

A bioconversion medium was prepared by combining 10 millimoles of guanosine and 10 millimoles of 1,2,4-triazole-3-carboxamide with 10 millimoles of $KH_2PO_4$ in 100 mL of water in a 500 mL flask at 70° C. Forty grams of cell paste were then added, followed next by 90 millimoles of guanosine and 90 millimoles of 1,2,4-triazole-3-carboxamide and finally by 10 millimoles of $KH_2PO_4$ 100 mL water at room temperature. The reaction mixture was vigorously stirred during this preparation with a top-driven laboratory stirrer.

The resulting reaction mixture was of a pasty consistency but did not gel. Production of ribavirin was similar to that of Example 2.

The invention has been described in detail with particular reference to preferred embodiments thereof, but it will be understood that variations and modifications an be effected within the spirit and scope of the invention.

I claim:

1. In a method for the production of a 1,2,4-triazole nucleoside comprising the step of reacting a ribose donor with a triazole compound in the presence of an enzyme preparation derived from Brevibacterium acetylicum, the improvement wherein the ribose donor is guanosine or a guanosine derivative; the concentration of the donor is above about 100 mM; said triazole compound is present in the amount of at least 100 mM; and the enzyme preparation is added 2. The method according to claim 1 comprising the additional steps of separating the enzyme preparation from the reaction mixture, washing the enzyme preparation and recovering the nucleoside from the wash fluid.

3. The method according to claim 1 comprising the additional step of adding ribose donor and triazole compound during the course of the reaction.

4. The method according to claim 1 wherein the enzyme preparation comprises cells of Brevibacterium acetylicum.

5. The method according to claim 1 wherein said triazole compound is 1,2,4-triazole-3-carboxamide.

6. The method according to claim 1 wherein said 1,2,4-triazole nucleoside is 1-$\beta$-D-ribofuranosyl-1,2,4-triazole-3-carboxamide.

* * * * *